United States Patent [19]

Borsanyi

[11] Patent Number: 4,867,744
[45] Date of Patent: * Sep. 19, 1989

[54] PERISTALTIC LINEAR PUMP WITH CONTOURED ROLLERS

[75] Inventor: Alexander S. Borsanyi, Newport Beach, Calif.

[73] Assignee: Baxter International Inc., Deerfield, Ill.

[*] Notice: The portion of the term of this patent subsequent to Nov. 13, 2001 has been disclaimed.

[21] Appl. No.: 52,600

[22] Filed: May 21, 1987

[51] Int. Cl.[4] .................................. A61M 5/00
[52] U.S. Cl. ..................... 604/153; 128/DIG. 12
[58] Field of Search ............... 604/67, 153, 152, 151; 417/474, 477, 476; 128/DIG. 12

[56] References Cited

U.S. PATENT DOCUMENTS

| | | | |
|---|---|---|---|
| 1,874,667 | 8/1931 | Wada | 417/474 |
| 2,483,924 | 10/1949 | Moulinier | 604/153 |
| 3,609,069 | 9/1971 | Martinelli | 417/474 |
| 3,981,633 | 9/1976 | Wall | 417/474 |
| 3,990,444 | 11/1976 | Vial | 604/153 |
| 4,373,525 | 2/1983 | Kobayashi | 417/474 |
| 4,482,347 | 11/1984 | Borsanyi | 604/153 |
| 4,617,014 | 10/1986 | Cannon et al. | 604/67 |

FOREIGN PATENT DOCUMENTS

| | | | |
|---|---|---|---|
| 2475645 | 8/1981 | France | 604/151 |
| 2492902 | 4/1982 | France | 604/151 |

Primary Examiner—John D. Yasko
Attorney, Agent, or Firm—Debra E. Dahl; John B. Lungmus

[57] ABSTRACT

A peristaltic pump equipped with a series of rollers eccentrically mounted upon a drive shaft, the pump also includes an elastomeric fluid delivery tube supported to extend in a direction parallel with the axis of the drive shaft. Each roller has a generally cylindrical outer surface equipped with a concentric annular rim that projects radially outwardly beyond the cylindrical surface and is rounded and smoothly tapered when viewed in longitudinal section. The rims of successive rollers are equally spaced and the rim diameter of each eccentric roller is sufficiently large to occlude a section of the tube when that roller is at its perigee with respect to the tube, at which time the adjacent cylindrical surface of the same roller also engages the tube but causes only limited non-occlusive deformation of that tube. The apparatus is particularly useful as a blood pump.

13 Claims, 1 Drawing Sheet

PERISTALTIC LINEAR PUMP WITH CONTOURED ROLLERS

BACKGROUND

U.S. Pat. No. 4,482,347 discloses a peristaltic pump which, because of its compactness and simplicity of construction, and its precise, accurate, and reliable operation, is particularly suitable for medical use. The pump includes a series of roller assemblies each having concentric inner and outer bearing members capable of free rotation with respect to each other. The inner members are concentrically mounted on a power drive shaft with the centers of the inner members equidistant from the axis of the shaft and spaced at uniform angular distances thereabout to describe a helix about the axis of the drive shaft. A resilient tube extends along a line parallel with the shaft and is supported by a platen so that the tube is sequentially compressed by each of the outer bearing members of the series of roller assemblies, thereby driving fluid through the resilient tube. A thin elastomeric membrane is interposed between the outer bearing members and the tube with the membrane in continuous contact with the tube during pump operation.

The outer surface of each outer bearing member of U.S. Pat. No. 4,482,347 is of uniform diameter for its full axial extent—that is, the outer surface appears as a straight line when each roller assembly is viewed in longitudinal (axial) section. In the construction of other types of pumps, particularly pumps in which rollers are urged lengthwise along compressible fluid-carrying tubes, it has been known to utilize rollers with contoured surfaces for improving tracking and for other purposes. Thus, U.S. Pat. No. 3,567,345 discloses a rotary pump having rollers with depressions 32, and U.S. Pat. No. 4,229,299 discloses a similar rotary pump having rollers with convex surfaces 300, 306.

U.S. Pat. No. 4,373,525 discloses a peristaltic pump with reciprocating fingers that engage a tube supported by a spring-loaded pressure plate. Each of the fingers is in the form of a rectangular plate (FIG. 3) having a rounded lower edge when viewed in elevation (FIG. 1).

SUMMARY OF THE INVENTION

One aspect of this invention lies in the discovery that important advantages are achieved if the outer surfaces of the rollers of a peristaltic pump of the general type depicted in patent 4,482,347 are contoured so that each roller has both a generally cylindrical outer surface portion and a concentric annular rim portion that projects radially outwardly beyond the cylindrical surface. The rim preferably has rounded sloping surfaces when viewed in longitudinal section, and its axial dimension should be substantially less than that of the adjacent cylindrical surface. The roller is dimensioned so that only the relatively narrow rim compresses the tube sufficiently to occlude its lumen during a brief interval in each cycle of shaft rotation and, although the cylindrical surface also compresses the tube, its diameter is not great enough to occlude the lumen. Each roller assembly is oriented so that one of its ends faces upstream and the other faces downstream, with the rims of successive rollers of the series being uniformly spaced axially apart.

During pump operation, the rim portion of each roller assembly successively compresses the elastomeric tube to drive fluid through its lumen and, in that respect, the operation is similar to that disclosed in U.S. Pat. No. 4,482,347. However, since compression of the tube to a sufficient extent, and with sufficient force, to occlude its lumen is limited to the zones of deformation produced by the relatively narrow rim portions of each roller assembly, the contoured roller construction imposes relatively low torque requirements on the power drive of the pump. This is particularly advantageous where the pump assembly is of small scale, battery-powered, and designed for any of a variety of medical applications. Where the pump is intended for use in pumping blood, the configuration of the rollers achieves an additional result of major importance—that of reducing damage to blood cells that might otherwise be caused by action of the pump. Since the zones of tube occlusion produced by all of the rollers taken in combination total only a minor portion of the axial length of the series of rollers, the cells exposed to injury because of forceful tube occlusion is substantially less than if occlusion occurred because of compressive forces exerted along the full axial dimension of each roller.

Other features, advantages, and objects of the invention will become apparent from the specification and drawings.

DRAWINGS

DETAILED DESCRIPTION OF PREFERRED EMBODIMENT

Figure 1:
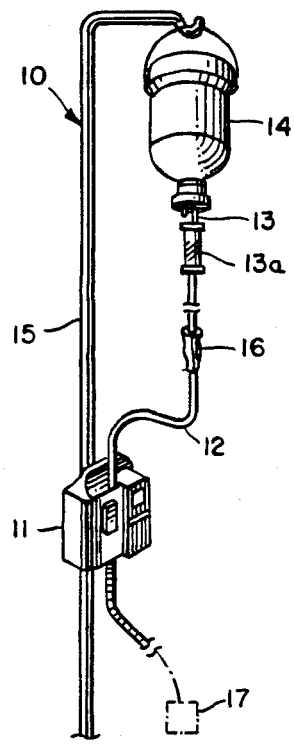
FIG. 1 is a perspective view of a system utilizing a peristaltic fluid-pumping apparatus of the invention for the infusion of blood.

Referring to the drawings, the numeral 10 generally designates an apparatus including a pump 11, a fluid delivery tube 12, coupling means 13 for coupling one end of the tube to a suitable container 14, in this case a blood container supported by a conventional IV stand 15. The coupling means takes the form of a spike formed as part of a drip chamber housing 13a and received within the opening of a vent-providing stopper at the mouth of the container. A suitable valve or clamp 16 may be provided for controlling or interrupting the flow of fluid through tube 12.

The opposite end of the tube 12 leads to a suitable connector 17 represented diagrammatically in FIG. 1. In the case of a fluid administration system, the connector would ordinarily take the form of a hypodermic needle or cannula. Excluding pump 11, the elements of the system shown in FIG. 1 are conventional and well known and, therefore, further discussion of such elements is believed unnecessary herein.

Except for certain features described in detail herein, pump 11 may be similar in construction and operation to the pump described in U.S. Pat. No. 4,482,347, the disclosure of which is incorporated herein by reference. The pump mechanism includes a series of bearing assemblies 18 each having inner and outer bearing members 19 and 20, respectively. Preferably, the inner bearing member takes the form of an inner bearing race, the outer member constitutes an outer race, and anti-friction bearing elements 21 are disposed therebetween. Such anti-friction bearing elements would normally consist of ball bearings, but the use of various types of roller bearings is possible. Furthermore, other types of bearing assemblies, such as self-lubricating sleeve bearings, might advantageously be used.

Each inner race or member 19 is eccentrically mounted upon a drive shaft 22 and the shaft is in turn journaled in brackets or mounting elements 23 and 24. One end of the shaft is operatively connected to power means in the form of a motor 25.

Each inner bearing member 19 is eccentrically mounted upon shaft 22 with the centers of all such members being equidistant from the axis 26 of the drive shaft and with the angular spacing between all of such centers being essentially the same and the sum of the angular spacing being 360°. Where a series of seven roller assemblies is provided as shown, the incremental angular distance between the centers of the inner members should be 360° divided by 7, or approximately 51.43°. A greater or smaller number of roller assemblies may be provided, although the preferred range is believed to be 3 to 30 such assemblies. The roller assemblies must be mounted upon the drive shaft so that the centers of the inner bearing members describe a spiral or helix of at least 360° about the drive shaft axis.

The inner bearing members 19 may be secured upon the shaft 22 in any suitable manner. In the embodiment illustrated, shaft 22 has a central portion 22a of non-circular (heptagonal) cross sectional outline and the eccentrically-disposed openings 19a in the respective inner bearing members 19 are of the same configuration so that the eccentric bearing members may be incrementally positioned upon the shaft with their centers helically oriented. The inner bearing members are thereby secured against independent relative rotation with respect to shaft 22, and locking elements 27 are secured to the shaft at opposite ends of the series of roller assemblies to hold the series against axial displacement.

A central portion of the flexible and deformable tube 12 is supported with its longitudinal axis parallel with the rotational axis of shaft 22. Ideally, the tube is stretched so that it is under slight axial tension, thereby assuring that the portion of the tube opposite the roller assemblies will be straight or linear in the absence of lateral distorting forces. For purposes of such tensioning, and to insure parallel alignment of the tube with the axis of the drive shaft 22, mounting clips or brackets may be located at 28 to immobilize those portions of the tube with respect to pump housing 29.

Figure 2:
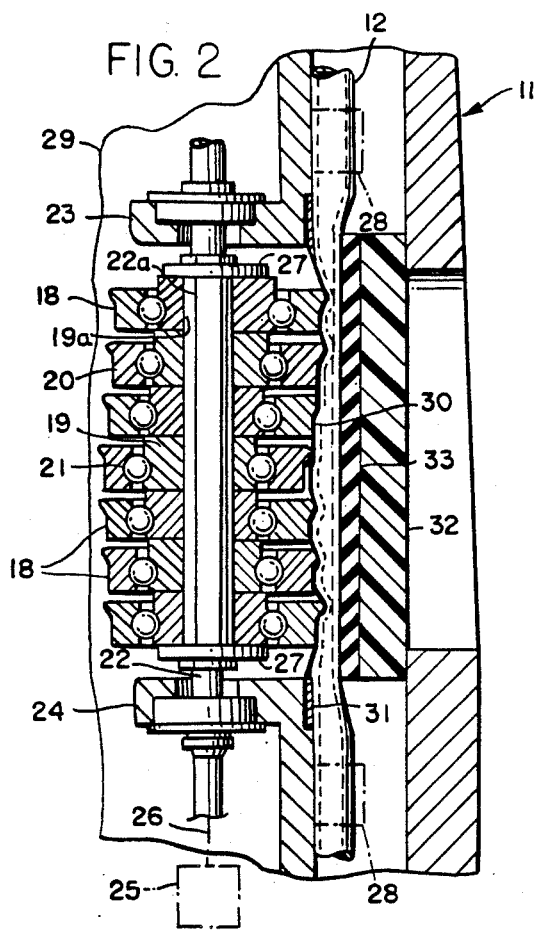
FIG. 2 is a vertical sectional view showing the primary fluid-pumping elements of the apparatus.

An elastomeric imperforate membrane 30 may be interposed between tube 12 and outer bearing members 20. The membrane is planar in an untensioned state and assumes the configuration shown in FIGS. 2-4 because of the distortions developed by roller assemblies 18 and tubing 12. It bridges the space in which the series of roller assemblies is located and separates that mechanism from tube 12. Any suitable means may be used to secure the periphery of the membrane to housing 29; in the embodiment illustrated, a frame 31 is secured to the housing by screws or any other attachment means and clamps the perimeter of the membrane tightly in place.

A rigid platen 32 braces tube 12 and not only maintains the tube in contact with one surface of the membrane 30 but also maintains the opposite surface of the membrane in contact with the outer bearing members 20 of assemblies 18. To reduce torque peaks that develop as each roller assembly attains its perigee in relation to tube 12, especially when two such assemblies (the first and last of the series) simultaneously compress and close the tube, platen 32 may be provided with a resilient facing 33 engaging and supporting tube 12. The facing must not be so compliant that it will allow outward displacement of the tube in preference to complete occlusion of that tube. The tube should close as shown most clearly in FIG. 3, with the resilience of facing 33 serving the primary purpose of reducing the torque peak once such occlusion has taken place. Additionally, the resilient facing may perform a secondary function of providing additional resistance to lateral or transverse displacement of those portions of the tube 12 being compressed by the eccentric roller assemblies 18.

Figure 3:
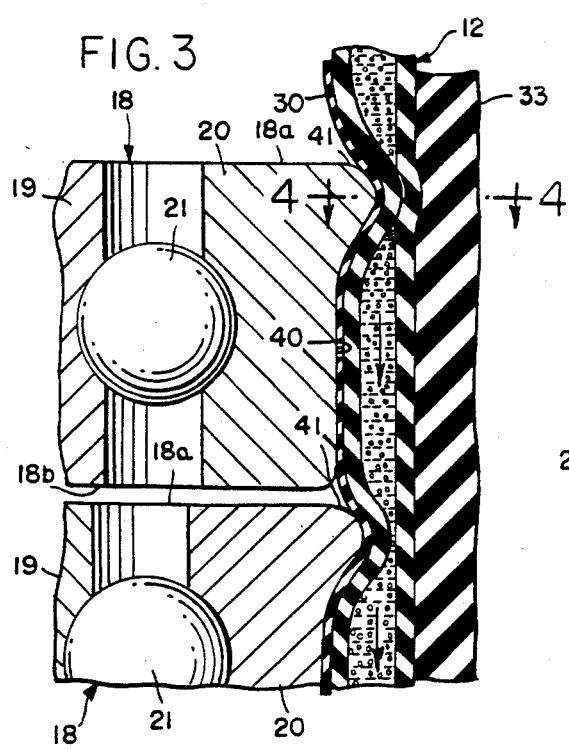
FIG. 3 is a greatly enlarged fragmentary vertical sectional view showing a pair of rollers in contact with the elastomeric tube of the pump.
Figure 4:
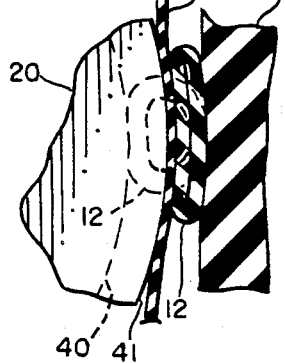
FIG. 4 is a fragmentary cross sectional view taken along line 4—4 of FIG. 3.
Figure 5:
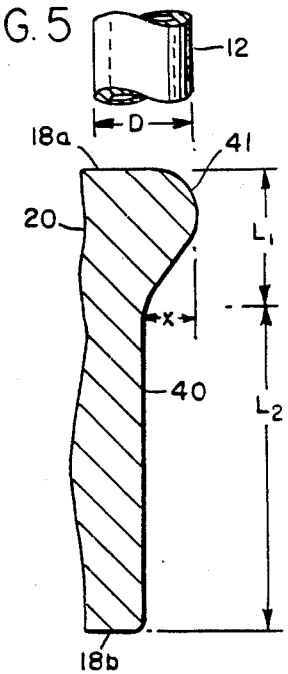
FIG. 5 is a schematic view illustrating certain size relationships of the fluid-pumping elements.

Each roller assembly 18 is oriented so that one end 18a faces upstream and the opposite end 18b faces downstream in relation to the flow of fluid through tube 12. As depicted most clearly in FIGS. 3-5, the outer bearing member of each roller assembly has a distinctive surface contour characterized by a generally cylindrical outer surface 40 and a concentric annular rim 41 that projects radially outwardly beyond the cylindrical surface. When viewed in longitudinal section, the rim 41 of each outer bearing member 20 is rounded (FIGS. 3, 5). The diameter of the annular rim is sufficient to cause complete occlusion of the tube 12 when the eccentrically-mounted roller assembly 18 is at its perigee in relation to tube 12 and platen 32. In contrast, the cylindrical surface 40 has a diameter sufficient only to cause non-occlusive deformation of the tube at such perigee but nevertheless great enough to expel a substantial proportion of the liquid volume of the tube section so deformed thereby (FIGS. 3, 4).

More specifically, the difference x between the diameters of the rim 41 and the cylindrical surface 40 is substantially less than the outside diameter D of tube 12 when the tube is in an undeformed state. Such a relationship means that when each roller assembly 18 is in a tube-occluding position, with its rim 41 compressing tube 12 to block the flow of fluid through the lumen thereof (as represented by the upper roller assembly 18 in FIG. 3), the cylindrical surface 40 of the same roller assembly will partially compress the tube but not to the point of occluding the lumen of that tube.

It will also be observed that the axial dimension $L_1$ of each rounded rim 41 is substantially less than the axial dimension $L_2$ of cylindrical surface 40. More specifically, $L_1$, should be no greater than about 75% of $L_2$ and preferably should fall within the range of about 2% to 50% of $L_2$. In the construction illustrated, $L_1$ is approximately 40% of $L_2$ or 30% of the combined length of $L_1$ and $L_2$. The result is that occlusive compression of the tube 12 occurs only along a small fraction of the total axial dimension of each roller assembly, especially because only the extreme outermost portion of each rounded rim 41—a portion of even lesser axial extent than $L_1$—is responsible for producing such occlusion (FIG. 3). The force necessary to produce such occlusion is therefore considerably less than if the zone of occlusion extended the full axial dimension of each outer bearing member 20. The torque peak is correspondingly reduced, resulting in a pump assembly requiring less power for its operation. Since the power requirements are relatively low, the construction is ideally suited for medical applications where fluids are to be administered intravenously over extended periods by small battery-powered pumps. If such a pump is sufficiently miniaturized, it may be readily portable, even wearable, as in the case of pumps for the infusion of insulin or other therapeutic agents to patients requiring such treatment.

The construction is particularly advantageous where the device is to serve as a blood pump because the limited areas of tube compression resulting from the distinctive surface contour of roller assemblies has the effect of markedly reducing the volume of blood cells compressed between the inner surfaces of the tube with each rotation of the pump shaft. Cylindrical surface 40 engages and compresses the tube in a reproducible and controlled manner each time that surface reaches its perigee, but such compression, although important in assuring effective pumping action, is insufficient to occlude the tube in that area and, hence, is insufficient to risk cell damage. In general, performance of a pump embodying this invention is comparable to a well-known Sarns pump, a standard of comparison for pumps causing little or no cell damage in their operation.

While in the foregoing I have disclosed an embodiment of the invention in considerable detail for purposes of illustration, it will be understood by those skilled in the art that many of these details may be varied without departing from the spirit and scope of the invention.

I claim:

1. A peristaltic pump comprising a series of roller assemblies each having concentric inner and outer bearing members freely rotatable with respect to each other; a drive shaft; said inner bearing members being eccentrically mounted upon said drive shaft with the centers of said inner bearing members being equidistant from the axis of said drive shaft and spaced uniform angular distances thereabout to describe a helix about said axis; journal means rotatably supporting said drive shaft; power means for rotating said drive shaft; a straight, tube of flexible and deformable polymeric material generally parallel with the longitudinal axis of said shaft, and platen means supporting said tube for successive occlusive compression by said roller assemblies of said series to direct fluid longitudinally through said tube; wherein the improvement comprises said outer bearing member of each roller assembly having a generally cylindrical outer surface terminating at one end in a concentric annular rim projecting radially outwardly beyond said cylindrical surface; said rim of the outer bearing member of each roller assembly having a diameter sufficient to cause occlusion of said tube when said roller assembly is at its perigee in relation to said tube and platen means; and said cylindrical surface of each bearing member having a diameter sufficient only to cause non-occlusive deformation of said tube at said perigee.

2. The pump of claim 1 in which each roller assembly is oriented so that one end is located upstream and the other end is located downstream in relation to the flow of fluid through said tube; said rim of each roller assembly being located at the upstream end thereof.

3. The pump of claims 1 or 2 in which said rim is rounded when viewed in longitudinal section.

4. The pump of claims 1 or 2 in which said rim has an axial dimension less than that of said cylindrical surface.

5. The pump of claim 4 in which said rim has an axial dimension within the range of 2% to 50% of the axial dimension of said cylindrical surface.

6. The pump of claim 5 in which said rim is rounded when viewed in longitudinal section.

7. The pump of claims 1 or 2 in which the difference between the diameters of said rim and said cylindrical surface is substantially less than the undeformed outside diameter of said tube.

8. The pump of claim 1 in which said platen means is rigid and includes a resilient facing in contact with said tube.

9. A peristaltic blood pumping apparatus comprising a series of roller assemblies each having concentric inner and outer bearing members freely rotatable with respect to each other; a drive shaft; said inner bearing members being eccentrically mounted upon said drive shaft with the centers of said inner bearing members being equidistant from the axis of said drive shaft and spaced uniform angular distances thereabout to describe a helix about said axis; journal means rotatably supporting said drive shaft; power means for rotating said drive shaft; an elastomeric membrane alongside said series of roller assemblies; means supporting said membrane for tangential engagement with the outer bearing members along one side of said membrane; a straight, elongated elastomeric tube extending along and engaging the opposite side of said membrane; platen means for supporting said tube with the longitudinal axis thereof in spaced parallel relation with respect to the rotational axis of said drive shaft and in engagement with said membrane; said outer bearing member of each roller assembly having a generally cylindrical outer surface terminating at one end in a concentric annular rim projecting radially outwardly beyond said cylindrical surface; said rim of the outer bearing member of each roller assembly having a diameter sufficient to cause occlusive compression of said tube when said roller assembly is at its perigee relative to said tube and platen means; and said cylindrical surface of each bearing member having a diameter sufficient only to cause non-occlusive deformation of said tube at said perigee.

10. The apparatus of claim 9 in which said rim is rounded when viewed in longitudinal section.

11. The apparatus of claims 9 or 10 in which said rim has an axial dimension less than that of said cylindrical surface.

12. The apparatus of claim 11 in which said rim has an axial dimension within the range of 2% to 50% of the axial dimension of said cylindrical surface.

13. The apparatus of claims 9 or 10 in which the difference between the diameters of said rim and said cylindrical surface is substantially less than the undeformed outside diameter of said tube.

* * * * *